United States Patent [19]

Blackman et al.

[11] 4,020,181

[45] Apr. 26, 1977

[54] METHOD OF REPELLING INSECTS FROM DOMESTIC MAMMALS

[75] Inventors: Gerald Gordon Blackman; Michael Derek Matthewson, both of Berkhamsted, England

[73] Assignee: Burroughs Wellcome Co., Research Triangle Park, N.C.

[22] Filed: May 7, 1975

[21] Appl. No.: 575,195

[30] Foreign Application Priority Data

May 8, 1974 United Kingdom ............. 20224/74

[52] U.S. Cl. .................................................. 424/305
[51] Int. Cl.$^2$ ......................................... A61K 31/215
[58] Field of Search ................................... 424/305

[56] References Cited

UNITED STATES PATENTS 3,236,728  2/1966  Newallis ........................... 424/305

OTHER PUBLICATIONS

Elliott et al.–Chem. Abst. vol. 80 (1974) p. 132,901f.
Elliott et al.–Nature vol. 246 Nov. 16, 1973 pp. 169–170.

*Primary Examiner*—Sam Rosen
*Attorney, Agent, or Firm*—Donald Brown

[57] ABSTRACT

A method is provided of treating a domestic mammal for the prevention of minimization of infestation by insects of the order Diptera. The method comprises the application to the mammal of 3-phenoxybenzyl-2,2-dimethyl-3-(2,2-dichlorovinyl) cyclopropane-1-carboxylate (the compounds of formula I) or a formulation comprising a compound of formula I in intimate admixture with a carrier or diluent therefor.

15 Claims, No Drawings

METHOD OF REPELLING INSECTS FROM DOMESTIC MAMMALS

This invention concerns the new use of known compounds and formulations containing them.

Flies of the order Diptera are a source of concern in animal husbandry as troublesome pests of many domestic animals. Apart from infesting animal wounds with eggs which mature in the flesh, they transmit a variety of infectious diseases by biting the animals, and can cause weight loss and decrease in milk yield.

A variety of insecticides have been shown to be active against such flies, and some have found commercial application in preventing or limiting irritation of the animals. Such preparations have included DDT, pyrethrins, methoxychlor and diazinon, but all known remedies have at least one of the drawbacks of little or no repellant action on the flies, low insecticidal activity, and poor residual effects. A repellant effect of an insecticide is of particular importance in minimising or preventing the fly from attaching itself to the host thus decreasing the annoyance to the animal and the risk of infestation.

Pyrethrins in particular are recognised to have no commercial potential as repellents for biting flies and have further found little commercial application in the control of other arthropod ectoparasites of mammals such as cattle ticks, cattle and sheep lice, sheep keds, and sheep scab. Amongst the synthetic pyrethroid analogues of the pyrethrins the compound bioresmethrin (2-benzyl-4-furylmethyl d-trans chrysanthemate) is known to be outstanding as a kill insecticide as measured by for example results obtained upon topical application of the compound to adult houseflies (*Musca domestica*) but has been found to have only limited knock-down activity against these flies compared with that of pyrethrins.

The compound, 3-phenoxybenzyl-2,2-dimethyl-3-(2,2-dichlorovinyl) cyclopropane-1-carboxylate, and its optical and geometrical isomers, (hereinafter referred to as the compounds of formula I) are known to have insecticidal activity against a variety of insects including *Musca domestica* but have been found to be significantly less active against these flies both as regards knock-down and upon topical application than bioresmethrin.

It has now been found that the compounds of formula (I) provide, for domestic animals, a remarkable protective effect against attack by insects of the order Diptera, and that this effect includes a high repellant effect, an excellent insecticidal effect, and long residual protection of the host animals against infestation when the compounds of formula (I) are used at substantially lower doses than have hitherto been used for pyrethrins. In particular the compounds are very effective in protecting cattle against the stable fly (*Stomoxys calcitrans*); the horn fly (*Haematobia irritans*) and the buffalo fly (*Lyperosia exigua*).

The compounds of formula (I) may be used in the protection of a variety of animals against Diptera, including cattle, sheep, horses, and other ungulate mammals.

Pests which may be controlled by the use of compounds of formula (I) include Simulidae (eg. Simulium sp.), Tabanidae (eg. Tabanus sp.), Muscidae (eg. *Stomoxys calcitrans*, Glossina sp., Lyperosia sp., Haemetobia sp., and Hydrotaea sp.), Calliphoridae (e.g Lucilia sp., Chrysomyia sp., Calliphora sp. and Callitroga sp.) and Oestridae (eg. *Hypoderma bovis*, *H. lineatum*, and *Dermatobia hominus*).

The compounds of formula (I) may be used for protecting an animal against Diptera infestations by application of the compounds themselves or in a diluted form in known fashion, as a dip, a spray, a foam, a dust, a paste or grease, or a pour-on formulation. Dips are not applied per se, but the animals immersed in a dipping bath containing the dip wash. Sprays may be applied by hand or by means of a spray race or arch or automatic treadle. Dusts may be distributed over the animals by means of a powder gun or incorporated in perforated bags attached to trees or rubbing bars. Pastes and greases may be applied manually or distributed over the surface of an inert material against which animals rub and transfer the material to their skins. Pour-on formulations are dispensed as a unit of liquid of small volume onto the backs of animals such that all or most of the liquid is retained on the animals.

The compounds of formula (I) may be formulated either as formulations ready for use on the animals or as formulations requiring further dilution prior to application, but both types of formulations comprise a compound of formula (I) in intimate admixture with one or more carriers or diluents. The carriers may be liquid, solid or gaseous or comprise mixtures of such substances, and the compound of formula (I) may be present in a concentration of from 0.025 to 99% w/v depending upon whether the formulation requires further dilution.

Dusts may be prepared by intimate admixture of the chosen compound with a powdered solid inert carrier for example suitable clays, kaolin, talc, mica, starch and diatomaceous earths.

Sprays of a compound of formula (I) may comprise a solution in an organic solvent (eg. those listed below) or an emulsion in water (dip wash or spray wash) prepared in the field from an emulsifiable concentrate (otherwise known as a water miscible oil) which may also be used for dipping purposes. The concentrate preferably comprises a mixture of the active ingredient, an organic solvent and one or more emulsifiers. Solvents may be present in wide limits but preferably in an amount of from 20 to 60% w/v of the composition and may be selected from kerosene, ketones, alkanols, xylene, aromatic naphtha, and other solvents known in the formulating art. The concentration of emulsifiers may be varied within wide limits but preferably in the range of 5 to 25% w/v and are conveniently non-ionic surface active agents including polyoxyalkylene esters of alkyl phenols and polyoxyethylene derivatives of hexitol anhydrides.

Dip washes may be prepared not only from emulsifiable concentrates but also from wettable powders comprising a compound of formula I in intimate admixture with a dispersing agent and one or more surface active agents.

Greases (or ointments) may be prepared from vegetable oils, synthetic esters of fatty acids or wool fat together with an inert base such as soft paraffin. A compound of formula (I) is preferably distributed uniformly through the mixture in solution or suspension. Greases may also be made from emulsifiable concentrates by diluting them with an ointment base.

Pastes are also semi-solid preparations in which a compound of formula (I) may be present as an uniform dispersion in a suitable base such as soft or liquid paraffin or made on a non-greasy basis with glycerin, mucilage or a suitable soap. As greases and pastes are usually applied without further dilution they should contain the appropriate percentage of the compound of formula (I) required for treatment.

Aerosol sprays may be prepared as a simple solution of the active ingredient in the aerosol propellant and a co-solvent such as halogenated alkanes and the solvents referred to above, respectively. Pour-on formulations may be made as a solution or suspension of a compound of formula I in a liquid medium which also contains a viscous oil to minimize spreading of the formulation on the surface of the animals.

The concentration of the compound of formula (I) to be applied to an animal will vary according to the isomer chosen, the nature of the formulation and the likely infestation, but in general 0.025% to 1% w/v of the compound should be present in the applied formulation. For the control of biting flies, a weekly application by standard techniques of a solution or emulsion of 0.025 to 0.05% w/v has been found to provide satisfactory control. If the compound is to be applied at longer intervals then a concentration of 0.05 to 0.1% w/v is desirable. It will be understood that the amount of the compound deposited on an animal will vary according to the method of application, size of the animal, concentration of the compound in the applied formulation and the nature of the formulation.

Dusts, greases, pastes and aerosol formulations are usually applied in a random fashion as described above and concentrations of 0.5 to 1.0% w/v of a compound of formula (I) in the applied formulation may be used.

It will be appreciated from the foregoing that what we will claim may comprise any novel feature described herein, principally and not exclusively, for example:

a. A method of treating a domestic mammal for the prevention of minimisation of infestation by insects of the order Diptera which comprises application to the mammal of a non-toxic, infestation prevention or minimisation effective amount of 3-phenoxybenzyl-2,2-dimethyl-3-(2,2-dichlorovinyl)cyclopropane-1-carboxylate (as hereinbefore defined) or of a formulation comprising said compound in intimate admixture with a carrier or diluent therefor.

The following Examples illustrate the present invention and the manner in which it may be carried out but should not be construed as in any way constituting a limitation thereof. In the Examples, compound Ia refers to 3-phenoxybenzyl (±)cis-trans-2,2-dimethyl-3-(2,2-dichlorovinyl) cyclopropane-1-carboxylate. Other compounds of formula I include the (+)trans, (+)cis, (±)trans and the (±)cis isomers. These compounds may be made according to the description in Dutch Patent Specification No. 7307130.

EXAMPLE 1

Control of S. calcitrans

Groups of two matched Friesian steers were sprayed, each with one liter of compound Ia at 0.01%, 0.025% and 0.050% w/v. The pairs were exposed almost daily in a fly chamber after treatment to approximately 100 starved S. calcitrans. The numbers of flies landing on the steers was counted over a 7 minute observation period. Counts at 1 to 2 minutes after treatment were discarded and an average taken for the group over the 3–7 minute period.

| Days post treatment | Mean fly counts | | |
|---|---|---|---|
| | 0.01% | 0.025% | 0.05% |
| PRE | 27.1 | >24.1 | 25.4 |
| 1 | 10.9 | 4.6 | 5.9 |
| 2 | — | 4.9 | — |
| 4 | 10.7 | 5.2 | 4.7 |
| 5 | 17.1 | 8.4 | 5.5 |
| 6 | 16.5 | 7.2 | 6.0 |
| 7 | 13.4 | 8.1 | 8.0 |
| 8 | 13.1 | 10.7 | 6.7 |
| 11 | 8.3 | 8.6 | 7.0 |
| 12 | 16.6 | 13.1 | 7.6 |
| 13 | 14.7 | 10.8 | 14.3 |
| 14 | 25.0 | 15.6 | 11.7 |
| 15 | — | 18.2 | 13.4 |
| 18 | — | 12.2 | 11.7 |
| 19 | — | 17.7 | 17.1 |
| 20 | — | 20.1 | 15.1 |
| 21 | — | — | 17.5 |

Flies feeding in quantity were first noted at 5 days 0.01%, 14 days 0.025% and 13 days 0.05%. Protection afforded by 0.025% and 0.05% treatment appear similar; both are superior to the 0.01% treatment.

Flies were collected after exposure and retained for 24 hours to observe mortality:

| 0.01% | engorged flies | 50% at 6 days, 0% thereafter |
|---|---|---|
| | unengorged flies | 100% at 1 day, decrease to 0% at 13 days |
| 0.025% | engorged flies | 100% to 8 days decrease to 20% at 19 days |
| | unengorged flies | 100% to 8 days, decrease to 80% at 19 days |
| 0.05% | engorged flies | 100% to 6 days, 50% at 7 and 8 days, 100% at 11 and 12 days, decrease to 14% at 14 days |
| | unengorged flies | 100% to 18 days, 62% at 21 days. |

The control of unengorged flies is superior to that of engorged flies. An increase in concentration gives an increase in length of control.

| Example 2 - Miscible Oil Formulation | |
|---|---|
| Compound Ia | 21% w/w |
| Trimethyl Benzenes (Aromasol H) | 67% " |
| Alkyl Phenol Ethylene Oxide condensate of 8–12 mol. Ethylene Oxide | 4% " |
| Calcium Dodecyl Benzene Sulphonate | 8% " |

| Example 3 - Dust Formulation | |
|---|---|
| Compound Ia | 1% w/w |
| Talc | 99% " |

| Example 4 - Wettable Powder Formulation | |
|---|---|
| Compound Ia | 20% w/w |
| Diatomaceous Earth | 74% " |
| Sodium Salt Naphthalene Sulphonic Acid | 5% " |
| Alkyl Phenol Ethylene Oxide condensate 8–12 mol. | 1% " |

| Example 5 - Pour-On Formulation | |
|---|---|
| Compound Ia | 20% w/w |
| Trimethyl Benzenes | 20% " |
| Vegetable Oil | 60% " |

EXAMPLE 6

Containers

Each of the formulations of Examples 2 to 5 were packed in sealed containers, each container labelled with indications of the suitability of its contents to control an ectoparasite of a mammal, especially a Diptera infestation.

What we claim is:

1. A method of repelling insects of the order Diptera from a domestic mammal which comprises depositing on said mammal a non-toxic effective Diptera insect repellent amount of a compound, 3-phenoxybenzyl-2,2-dimethyl-3-(2,2-dichlorovinyl) cyclopropane-1-carboxylate or of a formulation comprising said compound in intimate admixture with a carrier or diluent therefor.

2. A method according to claim 1 wherein the mammal is an ungulate.

3. A method according to claim 2 wherein the mammal is selected from cattle, sheep or horses.

4. A method according to claim 1 wherein the insects are selected from Simulidae, Tabanidae, Muscidae, Caliphoridae or Oestridae.

5. A method according to claim 1 wherein the insects are selected from Tabanidae or Muscidae.

6. A method according to claim 1 wherein the insects are Muscidae.

7. A method according to claim 1 wherein the insects are selected from *Stomoxys calcitrans*, Haematobia sp. or Lyperosia sp.

8. A method according to claim 1 which comprises application to the mammal of a formulation as defined in claim 1.

9. A method according to claim 8 wherein the formulation contains 0.025% w/v of 1% w/v of 3-phenoxybenzyl-2,2-dimethyl-3-(2,2-dichlorovinyl) cyclopropane-1-carboxylate.

10. A method according to claim 8 wherein the carrier or diluent in the formulation is a solid or gas.

11. A method according to claim 10 wherein the formulation contains 0.5% w/v to 1.0% w/v of 3-phenoxybenzyl-2,2-dimethyl-3-(2,2-dichlorovinyl) cyclopropane-1-carboxylate.

12. A method according to claim 8 wherein the carrier or diluent in the formulation is a liquid.

13. A method according to claim 12 wherein the formulation contains 0.025% w/v to 0.1% w/v of 3-phenoxybenzyl-2,2-dimethyl-3-(2,2-dichlorovinyl) cyclopropane-1-carboxylate.

14. A method according to claim 13 wherein the formulation is reapplied to the mammal after an interval of one week.

15. A method according to claim 1 which comprises application to the mammal of 3-phenoxybenzyl (±)cis - trans - 2,2-dimethyl-3-(2,2-dichlorovinyl) cyclopropane-1-carboxylate or a formulation thereof.

* * * * *

REEXAMINATION CERTIFICATE (876th)
United States Patent [19]
Blackman et al.

[11] B1 4,020,181

[45] Certificate Issued Jun. 28, 1988

[54] METHOD OF REPELLING INSECTS FROM DOMESTIC MAMMALS

[75] Inventors: Gerald G. Blackman; Michael D. Matthewson, both of Berkhamsted, England

[73] Assignee: Burroughs Wellcome Co., Research Triangle Park, N.C.

Reexamination Request:
No. 90/001,172, Feb. 25, 1987

Reexamination Certificate for:
Patent No.: 4,020,181
Issued: Apr. 26, 1977
Appl. No.: 575,195
Filed: May 7, 1975

[30] Foreign Application Priority Data

May 8, 1974 [GB] United Kingdom ............... 20224/74

[51] Int. Cl.$^4$ ............................................. A61K 31/215

[52] U.S. Cl. .......................... 514/531; 424/DIG. 10
[58] Field of Search ............................... 514/531

[56] References Cited

FOREIGN PATENT DOCUMENTS 1413491 11/1975 United Kingdom .

OTHER PUBLICATIONS

West Sussex Gazett & South of England Advertiser, Nov. 29, 1973.
Chemistry and Industry–Dec. 21, 1974, pp. 978–980.

*Primary Examiner*—Sam Rosen

[57] ABSTRACT

A method is provided of treating a domestic mammal for the prevention of minimization of infestation by insects of the order Diptera. The method comprises the application to the mammal of 3-phenoxybenzyl-2,2-dimethyl-3-(2,2-dichlorovinyl) cyclopropane-1-carboxylate (the compounds of formual I) or a formulation comprising a compound of formula I in intimate admixture with a carrier or diluent therefor.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is cancelled.

Claims 2, 4–8 and 15 are determined to be patentable as amended.

Claims 3 and 9–14, dependent on an amended claim, are determined to be patentable.

New claims 16–20 are added and determined to be patentable.

2. A method according to claim [1] *16* wherein the mammal is an ungulate.

4. A method according to claim [1] *16* wherein the insects are selected from Simulidae, Tabanidae, Muscidae, Caliphoridae or Oestridae.

5. A method according to claim [1] *16* wherein the insects are selected from Tabanidae or Muscidae.

6. A method according to claim [1] *16* wherein the insects are Muscidae.

7. A method according to claim [1] *16* wherein the insects are selected from *Stomoxys calcitrans*, *Haematobia* sp. or *Lyperosia* sp.

8. A method according to claim [1] *16* which comprises application to the mammal of a formulation as defined in claim [1] *16*.

15. A method according to claim [1] *16* which comprises application to the mammal of 3-phenoxybenzyl (±) cistrans-2,2-dimethyl-3-(2,2-dichlorovinyl) cyclopropane-1-carboxylate or a formulation thereof.

*16. A method of protecting domestic mammals from infestation by insects of the order Diptera comprising*

*applying directly to the skin of said mammal a nontoxic effective Diptera insect repellent quantity of the compound 3-phenoxybenzyl-2,2-dimethyl-3-(2,2-dichlorovinyl) cyclopropane-1-carboxylate or a formulation comprising said compound in intimate admixture with a carrier or diluent therefor,*

*whereby an insect of the order Diptera is repelled away from said domestic mammal prior to attaching itself to the mammal.*

*17. A method of repelling insects of the order Diptera from a domestic mammal which comprises:*

*pouring onto the animal a formulation comprising vegetable oil, trimethyl benzene and a nontoxic effective Diptera insect repellant quantity of the compound 3-phenoxybenzyl-2,2-dimethyl-3-(2,2-dichlorovinyl) cyclopropane-1-carboxylate.*

*18. A method as set forth in claim 17, wherein said quantity of said compound comprises from 0.025 to 1 weight/volume percent.*

*19. A method as set forth in claim 18, wherein said trimethyl benzene comprises up to 20 weight/weight percent of said formulation.*

*20. A method of repelling insects of the order Diptera from a domestic mammal which comprises pouring on to the animal a formulation comprising a nontoxic effective Diptera insect repellent quantity of the compound 3-phenoxybenzyl-2,2-dimethyl-3-(2,2-dichlorovinyl) cyclopropane-1-carboxylate in intimate admixture with a carrier.*

* * * * *